United States Patent
Mayer et al.

(10) Patent No.: US 9,746,427 B2
(45) Date of Patent: Aug. 29, 2017

(54) DETECTION OF PLATING ON WAFER HOLDING APPARATUS

(71) Applicant: Novellus Systems, Inc., Fremont, CA (US)

(72) Inventors: Steven T. Mayer, Lake Oswego, OR (US); Haiying Fu, Camas, WA (US); Thomas Anand Ponnuswamy, Sherwood, OR (US); Bryan L. Buckalew, Tualatin, OR (US)

(73) Assignee: Novellus Systems, Inc., Fremont, CA (US)

( * ) Notice: Subject to any disclaimer, the term of this patent is extended or adjusted under 35 U.S.C. 154(b) by 710 days.

(21) Appl. No.: 14/178,804

(22) Filed: Feb. 12, 2014

(65) Prior Publication Data
US 2014/0230855 A1 Aug. 21, 2014

Related U.S. Application Data

(60) Provisional application No. 61/765,502, filed on Feb. 15, 2013.

(51) Int. Cl.
*G01N 21/00* (2006.01)
*G01N 21/95* (2006.01)
(Continued)

(52) U.S. Cl.
CPC ......... *G01N 21/9501* (2013.01); *C25D 21/12* (2013.01); *G01N 27/9046* (2013.01); *C25D 17/001* (2013.01); *C25D 17/06* (2013.01)

(58) Field of Classification Search
CPC ...... C25D 17/001; C25D 17/06; C25D 21/12; G01N 27/42; G01N 21/94; G01N 21/9501; C23C 16/0227
(Continued)

(56) References Cited

U.S. PATENT DOCUMENTS 3,430,055 A * 2/1969 Metzger ............ G01N 21/8901
250/224
3,684,633 A 8/1972 Haase
(Continued)

FOREIGN PATENT DOCUMENTS

CN 1550033 A 11/2004
CN 1623012 A 6/2005
(Continued)

OTHER PUBLICATIONS

U.S. Appl. No. 14/936,328, titled "Integrated Elastomeric Lipseal and Cup Bottom for Reducing Wafer Sticking," filed Nov. 9, 2015.
(Continued)

*Primary Examiner* — Hoa Pham
(74) *Attorney, Agent, or Firm* — Weaver Austin Villeneuve & Sampson LLP

(57) ABSTRACT

The embodiments herein relate to methods and apparatus for detecting whether unwanted metallic deposits are present on a bottom of a substrate holder used in an electroplating apparatus. The presence of such unwanted deposits is harmful to electroplating processes because the deposits scavenge current that is intended to cause electroplating on a substrate. When such current scavenging occurs, the electroplating results on the substrates are poor. For instance, features positioned near the edge of a substrate are likely to plate to an insufficient thickness. Further, where such current scavenging is great, the overall thickness of the material plated on the substrate may be too thin. As such, there is a need to detect when such unwanted deposits are present, such that plating under these poor conditions may be avoided. This detection will help preserve costly wafers.

21 Claims, 5 Drawing Sheets

(51) Int. Cl.
*C25D 21/12* (2006.01)
*G01N 27/90* (2006.01)
*C25D 17/00* (2006.01)
*C25D 17/06* (2006.01)

(58) Field of Classification Search
USPC .......................................... 356/237.1–237.5
See application file for complete search history.

(56) References Cited

U.S. PATENT DOCUMENTS

| | | |
|---|---|---|
| 3,716,765 A | 2/1973 | Rueffer et al. |
| 3,724,471 A | 4/1973 | Sitges |
| 4,418,432 A | 12/1983 | Vidal |
| 4,466,864 A | 8/1984 | Bacon et al. |
| 4,569,695 A | 2/1986 | Yamashita et al. |
| 4,924,891 A | 5/1990 | Soubrier et al. |
| 5,000,827 A | 3/1991 | Schuster et al. |
| 5,221,449 A | 6/1993 | Colgan et al. |
| 5,227,041 A | 7/1993 | Brogden et al. |
| 5,281,485 A | 1/1994 | Colgan et al. |
| 5,289,639 A | 3/1994 | Bard et al. |
| 5,311,634 A | 5/1994 | Andros |
| 5,482,611 A | 1/1996 | Helmer et al. |
| 5,519,945 A | 5/1996 | Ahvenniemi et al. |
| 5,723,028 A | 3/1998 | Poris |
| 5,853,559 A | 12/1998 | Tamaki et al. |
| 5,860,361 A | 1/1999 | Nanjyo et al. |
| 5,985,762 A | 11/1999 | Geffken et al. |
| 6,071,388 A | 6/2000 | Uzoh |
| 6,074,544 A | 6/2000 | Reid et al. |
| 6,080,291 A | 6/2000 | Woodruff et al. |
| 6,099,702 A | 8/2000 | Reid et al. |
| 6,108,847 A | 8/2000 | Cueman et al. |
| 6,110,346 A | 8/2000 | Reid et al. |
| 6,124,203 A | 9/2000 | Joo et al. |
| 6,126,798 A | 10/2000 | Reid et al. |
| 6,139,712 A | 10/2000 | Patton et al. |
| 6,156,167 A | 12/2000 | Patton et al. |
| 6,159,354 A | 12/2000 | Contolini et al. |
| 6,162,344 A | 12/2000 | Reid et al. |
| 6,176,985 B1 | 1/2001 | Downes, Jr. et al. |
| 6,179,973 B1 | 1/2001 | Lai et al. |
| 6,179,983 B1 | 1/2001 | Reid et al. |
| 6,193,854 B1 | 2/2001 | Lai et al. |
| 6,217,716 B1 | 4/2001 | Lai |
| 6,221,757 B1 | 4/2001 | Schmidbauer et al. |
| 6,251,238 B1 | 6/2001 | Kaufman et al. |
| 6,251,242 B1 | 6/2001 | Fu et al. |
| 6,261,433 B1 | 7/2001 | Landau |
| 6,267,860 B1 | 7/2001 | Brodsky |
| 6,270,646 B1 | 8/2001 | Walton et al. |
| 6,274,008 B1 | 8/2001 | Gopalraja et al. |
| 6,277,249 B1 | 8/2001 | Gopalraja et al. |
| 6,303,010 B1 | 10/2001 | Woodruff et al. |
| 6,309,520 B1 | 10/2001 | Woodruff et al. |
| 6,379,468 B1 | 4/2002 | Chang et al. |
| RE37,749 E | 6/2002 | Poris |
| 6,398,926 B1* | 6/2002 | Mahneke ................ C25D 7/12 204/224 R |
| 6,413,388 B1 | 7/2002 | Uzoh et al. |
| 6,436,249 B1 | 8/2002 | Patton et al. |
| 6,517,689 B1 | 2/2003 | Hongo et al. |
| 6,540,899 B2 | 4/2003 | Keigler |
| 6,551,487 B1 | 4/2003 | Reid et al. |
| 6,579,430 B2 | 6/2003 | Davis et al. |
| 6,589,401 B1 | 7/2003 | Patton et al. |
| 6,612,915 B1 | 9/2003 | Uzoh et al. |
| 6,613,214 B2 | 9/2003 | Dordi et al. |
| 6,627,052 B2 | 9/2003 | Fluegel et al. |
| 6,755,946 B1 | 6/2004 | Patton et al. |
| 6,755,954 B2 | 6/2004 | Mayer et al. |
| 6,773,560 B2 | 8/2004 | Pedersen et al. |
| 6,800,187 B1 | 10/2004 | Reid et al. |
| 6,869,510 B2 | 3/2005 | Woodruff et al. |
| 6,908,540 B2 | 6/2005 | Kholodenko |
| 7,033,465 B1 | 4/2006 | Patton et al. |
| 7,070,686 B2 | 7/2006 | Contolini et al. |
| 7,087,144 B2 | 8/2006 | Herchen |
| 7,522,055 B2 | 4/2009 | Carrender et al. |
| 7,935,231 B2 | 5/2011 | Ghongadi et al. |
| 7,985,325 B2 | 7/2011 | Rash et al. |
| 8,172,992 B2 | 5/2012 | Prabhakar et al. |
| 8,377,268 B2 | 2/2013 | Rash et al. |
| 8,398,831 B2 | 3/2013 | Ghongadi et al. |
| 9,221,081 B1 | 12/2015 | Mayer et al. |
| 9,228,270 B2 | 1/2016 | Feng et al. |
| 9,476,139 B2 | 10/2016 | Chua et al. |
| 2002/0000372 A1 | 1/2002 | Pedersen et al. |
| 2002/0084183 A1 | 7/2002 | Hanson et al. |
| 2002/0108851 A1 | 8/2002 | Woodruff et al. |
| 2002/0134403 A1 | 9/2002 | Selwyn et al. |
| 2002/0144900 A1 | 10/2002 | Keigler |
| 2002/0157686 A1 | 10/2002 | Kenny et al. |
| 2003/0010641 A1 | 1/2003 | Kholodenko |
| 2003/0085118 A1 | 5/2003 | Tench et al. |
| 2003/0085119 A1 | 5/2003 | Davis et al. |
| 2003/0134044 A1 | 7/2003 | Aoki et al. |
| 2003/0181349 A1 | 9/2003 | Maeno et al. |
| 2004/0002430 A1 | 1/2004 | Verhaverbeke |
| 2004/0060576 A1 | 4/2004 | Cronin et al. |
| 2004/0084301 A1 | 5/2004 | Dordi et al. |
| 2004/0112405 A1 | 6/2004 | Lee et al. |
| 2004/0149573 A1 | 8/2004 | Herchen |
| 2004/0171277 A1 | 9/2004 | Oh et al. |
| 2005/0081899 A1 | 4/2005 | Shannon |
| 2005/0183947 A1 | 8/2005 | Henuset |
| 2005/0218000 A1 | 10/2005 | Hafezi et al. |
| 2005/0284754 A1 | 12/2005 | Herchen et al. |
| 2005/0287928 A1 | 12/2005 | Hardikar et al. |
| 2006/0118132 A1 | 6/2006 | Bergman et al. |
| 2006/0151007 A1 | 7/2006 | Bergman |
| 2006/0226000 A1 | 10/2006 | Hanson et al. |
| 2006/0237308 A1 | 10/2006 | Herchen |
| 2006/0246690 A1 | 11/2006 | Dordi et al. |
| 2006/0266653 A1 | 11/2006 | Birang et al. |
| 2007/0077871 A1 | 4/2007 | Park et al. |
| 2007/0141849 A1 | 6/2007 | Kanno et al. |
| 2007/0199578 A1 | 8/2007 | Nomura et al. |
| 2008/0011322 A1 | 1/2008 | Weber et al. |
| 2008/0117051 A1 | 5/2008 | Carrender et al. |
| 2009/0009753 A1* | 1/2009 | Horai ..................... G01N 21/65 356/237.3 |
| 2009/0033889 A1* | 2/2009 | Bleeker ............... G03F 7/70866 355/30 |
| 2009/0107835 A1 | 4/2009 | Ghongadi et al. |
| 2009/0107836 A1 | 4/2009 | Rash et al. |
| 2009/0117730 A1 | 5/2009 | Maitani et al. |
| 2010/0116290 A1 | 5/2010 | Zhu et al. |
| 2010/0144158 A1* | 6/2010 | Ito ..................... H01L 21/67051 438/758 |
| 2010/0155254 A1 | 6/2010 | Prabhakar et al. |
| 2011/0181000 A1 | 7/2011 | Ghongadi et al. |
| 2011/0233056 A1 | 9/2011 | Rash et al. |
| 2012/0043200 A1 | 2/2012 | Fujikata et al. |
| 2012/0181170 A1 | 7/2012 | Prabhakar et al. |
| 2013/0042454 A1 | 2/2013 | Feng et al. |
| 2013/0256146 A1 | 10/2013 | Chua et al. |
| 2013/0292254 A1 | 11/2013 | Kumar et al. |
| 2014/0230855 A1* | 8/2014 | Mayer ................ G01N 21/9501 134/18 |
| 2014/0367265 A1* | 12/2014 | Ravid .................... G01B 7/105 205/83 |
| 2015/0218726 A1 | 8/2015 | Feng et al. |
| 2016/0145761 A1 | 5/2016 | Mayer et al. |
| 2016/0186355 A1 | 6/2016 | Feng et al. |
| 2016/0201212 A1 | 7/2016 | Ostrowski et al. |

(56) References Cited

U.S. PATENT DOCUMENTS

| | | | |
|---|---|---|---|
| 2017/0009369 | A1 | 1/2017 | Berke et al. |
| 2017/0009370 | A1 | 1/2017 | Chua et al. |

FOREIGN PATENT DOCUMENTS

| | | | |
|---|---|---|---|
| CN | 1930666 | A | 3/2007 |
| CN | 101599420 | | 12/2009 |
| CN | 101798698 | | 8/2010 |
| EP | 1 724 820 | A1 | 11/2006 |
| JP | 2002-069698 | | 3/2002 |
| JP | 2002-540011 | | 11/2002 |
| JP | 2004-83932 | | 3/2004 |
| JP | 2004-247738 | | 9/2004 |
| JP | 2004-270014 | | 9/2004 |
| JP | 2008-95157 | | 4/2008 |
| JP | 2010-150659 | | 7/2010 |
| KR | 10-2004-0079843 | | 9/2004 |
| KR | 10-2004-0081577 | | 9/2004 |
| KR | 10-2005-0068038 | | 7/2005 |
| KR | 10-2008-0007931 | | 1/2008 |
| TW | 544811 | | 8/2003 |
| TW | 200409836 | | 6/2004 |
| TW | 200410296 | A | 6/2004 |
| TW | 200511422 | A | 3/2005 |
| TW | I244548 | | 12/2005 |
| WO | WO 99/41434 | | 8/1999 |
| WO | WO 03/006718 | | 1/2003 |
| WO | WO 2013/148890 | | 10/2013 |

OTHER PUBLICATIONS

U.S. Appl. No. 15/004,593, titled "Durable Low Cure Temperature Hydrophobic Coating in Electroplating Cup Asssembly," filed Jan. 22, 2016.
US Office Action, dated Nov. 6, 2014, issued in U.S. Appl. No. 13/563,619.
US Final Office Action, dated Apr. 23, 2015, issued in U.S. Appl. No. 13/563,619.
US Notice of Allowance, dated Aug. 31, 2015, issued in Application No. 13/563,619.
US Notice of Allowance [corrected Notice of Allowability], dated Sep. 23, 2015, issued in U.S. Appl. No. 13/563,619.
US Office Action, dated Feb. 23, 2015, issued in U.S. Appl. No. 13/584,343.
US Notice of Allowance, dated Aug. 31, 2015, issued in U.S. Appl. No. 13/584,343.
US Notice of Allowance, dated Jun. 30, 2016, issued in U.S. Appl. No. 13/853,935.
US Office Action, dated Oct. 28, 2015, issued in U.S. Appl. No. 13/852,767.
US Final Office Action, dated Apr. 28, 2016, issued in U.S. Appl. No. 13/852,767.
Chinese First Office Action dated Jan. 26, 2016, issued in Application No. CN 201210289735.1.
Japanese First Office Action dated Jun. 28, 2016, issued in Application No. JP 2012-179853.
Singapore Search Report and Written Opinion, dated Oct. 6, 2014, issued in Application No. SG 201206129-7.
Singapore Final Exam Report, dated May 20, 2015, issued in Application No. SG 201206129-7.
Taiwan Office Action and Search Report, dated May 12, 2016, issued in Application No. TW 101129602.
PCT International Preliminary Report on Patentability and Written Opinion dated Oct. 9, 2014 issued in PCT/US2013/034178.
Chinese First Office Action dated Mar. 2, 2016 issued in Application No. CN 201380023757.6.
*Cambridge English Dictionary*, Meaning of "against" (2016), 2 pages.
Everett, D.H. (2001) "Definition of Surface Active Agents," *Manual of Symbols and Terminology for Physicochemical Quantities and Units*, Appendix II, *International Union of Pure and Applied Chemistry, Division of Physical Chemistry*, Adopted by the IUPAC Council at Washington DC, USA on Jul. 23, 1971, 6pp.
U.S. Appl. No. 13/563,619, titled "Automated Cleaning of Wafer Plating Assembly," filed Jul. 31, 2012.
US Office Action, dated Nov. 1, 2011, issued in U.S. Appl. No. 12/633,219.
US Notice of Allowance, dated Jan. 12, 2012, issued in U.S. Appl. No. 12/633,219.
US Notice of Allowance, dated Mar. 19, 2012, issued in U.S. Appl. No. 12/633,219.
US Office Action, dated Oct. 26, 2012, issued in U.S. Appl. No. 13/432,767.
US Final Office Action, dated Nov. 26, 2013, issued in U.S. Appl. No. 13/432,767.
US Office Action, dated Mar. 2, 2011, issued in U.S. Appl. No. 11/929,638.
US Notice of Allowance, dated May 23, 2011, issued in U.S. Appl. No. 11/929,638.
US Office Action, dated Jul. 7, 2010, issued in U.S. Appl. No. 11/932,595.
US Office Action, dated Nov. 17, 2010, issued in U.S. Appl. No. 11/932,595.
US Notice of Allowance, dated Jan. 26, 2011, issued in U.S. Appl. No. 11/932,595.
US Notice of Allowance, dated Mar. 8, 2011, issued in U.S. Appl. No. 11/932,595.
US Notice of Allowance (Supplemental Notice of Allowability) dated Mar. 11, 2011, issued in U.S. Appl. No. 11/932,595.
US Notice of Allowance, dated Mar. 18, 2011, issued in U.S. Appl. No. 11/932,595.
US Office Action, dated Nov. 4, 2011, issued in U.S. Appl. No. 13/154,224.
US Office Action, dated Mar. 16, 2012, issued in U.S. Appl. No. 13/154,224.
US Final Office Action, dated Jul. 18, 2012, issued in U.S. Appl. No. 13/154,224.
US Notice of Allowance, dated Oct. 4, 2012, issued in U.S. Appl. No. 13/154,224.
US Notice of Allowance (Corrected Notice of Allowability) dated Jan. 23, 2013, issued in U.S. Appl. No. 13/154,224.
US Office Action, dated May 21, 2012, issued in U.S. Appl. No. 13/079,745.
US Office Action, dated Sep. 21, 2012, issued in U.S. Appl. No. 13/079,745.
US Notice of Allowance, dated Nov. 19, 2012, issued in Application No. 13/079,745.
Chinese First Office Action dated May 2, 2013 issued in CN 200910211989.X.
Japanese Office Action, dated Oct. 2, 2012, issued in Application No. 2009-278998.
Korean Description of Notification of Provisional Rejection, dated May 10, 2012, issued in Application No. 2009-0122738.
Korean Notification of Decision to Grant, dated Sep. 4, 2012, issued in Application No. 2009-0122738.
Singapore Written Opinion, dated Mar. 4, 2011, issued in Application No. 200908245.4.
Singapore Search and Examination Report, dated Oct. 10, 2011, issued in Application No. 200908245.4.
Taiwan International Search Report, dated Jun. 11, 2012, issued in Application No. 098142112.
PCT International Search Report and Written Opinion dated Jul. 25, 2013 issued in PCT/US2013/034178.
Shin-Etsu Polymer Co., Ltd., "L-type connector," http://www.shinpoly.co.jp./business/connector/products_e/l/html?typezeb (one page) downloaded May 23, 2003.
Shin-Etsu Polymer Co., Ltd., "SS-type connector," http://www.shinpoly.co.jp./business/connector/products_e/ss.html?typezeb (2 pages) downloaded May 23, 2003.
Chinese Second Office Action dated Nov. 2, 2016, issued in Application No. CN 201210289735.1.
Chinese Second Office Action dated Jan. 24, 2017 issued in Application No. CN 201380023757.6.

(56) References Cited

OTHER PUBLICATIONS

Taiwan Examination and Search Report dated Oct. 12, 2016, issued in TW 102111233.
Chinese First Office Action dated Jun. 20, 2017 issued in CN 201510837221.9.
U.S. Appl. No. 15/638,131, filed Jun. 29, 2017, Arora et al.

* cited by examiner

DETECTION OF PLATING ON WAFER HOLDING APPARATUS

CROSS REFERENCE TO RELATED APPLICATION

This application claims benefit of U.S. Provisional Patent Application Ser. No. 61/765,502, filed Feb. 15, 2013, and titled "DETECTION OF PLATING ON WAFER HOLDING APPARATUS," which is herein incorporated by reference in its entirety and for all purposes.

BACKGROUND

Recent advances in semiconductor fabrication and processing has led to increased use of electroplating to deposit a variety of materials on semiconductor devices. Such materials include electroplated copper, nickel, and tin-silver alloys. Electroplating tin-silver alloys oftentimes leads to spurious metal buildup around the lip seal and cup regions of a substrate holder assembly (sometimes implemented as a clamshell assembly). This buildup, referred to as "lip seal plating" and/or "cup bottom plating," depending on its location, may in some circumstances cause the seal between the substrate and lip seal to fail, resulting in contamination of inner portions of the clamshell assembly with potentially corrosive electroplating solution. Further, when either lip seal or cup bottom plating occurs, the uniformity and quality of plating on the wafer may be significantly decreased, and some sort of remedial action is generally necessary before more wafers can be plated effectively. There exists a need for a method of detecting normal operational excursions such as when lip seal plating and cup bottom plating are present, in order to avoid processing costly wafers under sub-standard plating conditions.

SUMMARY

The disclosed embodiments relate to methods and apparatus for detecting the presence of unwanted metallic deposits on the bottom of a substrate holder used in an electroplating apparatus. Such detection is useful because the presence of unwanted deposits can have a harmful effect on electroplating results. In one aspect of the disclosed embodiments, a method for detecting the presence or absence of metal deposits on a substrate holder of an electroplating apparatus is provided, including: positioning detection hardware proximate the substrate holder of the electroplating apparatus, where the substrate holder is an annular element having a bottom and an interior edge, and where the substrate holder is configured to support a substrate during electroplating; and operating the detection hardware to detect the presence or absence of metal deposits in a detection region on the substrate holder, wherein the detection region is an annular region on the bottom of the substrate holder that extends at least about 5 mm or more from the interior edge of the substrate holder.

In some embodiments, the deposits include metals having significantly different reduction potentials. In a particular example, the deposits include tin and silver. Operating the detection hardware may occur on a schedule. In some cases, operating the detection hardware occurs after a certain number of substrates have been processed using the substrate holder, after a certain amount of charge has passed during deposition on substrates using the substrate holder, or after a certain amount or thickness of metal has been deposited on substrates using the substrate holder. In another example, operating the detection hardware occurs after the substrate holder is cleaned, for example after each time the substrate holder is cleaned. The detection region may be an annular region on the bottom of the substrate holder. In various cases, the detection region extends at least about 5 mm from the interior edge of the substrate holder. For instance, the detection region may extend about 10 mm or greater, or about 15 mm or greater, or about 20 mm or greater from the interior edge of the substrate holder, on the bottom of the substrate holder.

In certain cases, operating the detection hardware may include shining a source light on the detection region of the substrate holder and measuring a reflected light that reflects off the detection region of the substrate holder. Shining a light source on the detection region of the substrate holder may include shining a light that is complementary in color to a color of the detection region. In another case, operating the detection hardware may include: flowing an alternating current through a circular primary excitation coil positioned near the detection region to thereby generate a changing magnetic field that interacts with the detection region to produce eddy currents; and monitoring the phase and/or magnitude of the eddy currents to detect the presence or absence of metal deposits. The monitoring may be done with a receiver coil that is distinct from the primary excitation coil, in some cases. In other cases, the monitoring may be done by measuring changes to the alternating current flowing through the primary excitation coil. In further embodiments, operating the detection hardware may include: providing two or more electrical contacts that contact the detection region, where there is an electrical connection between the two or more electrical contacts; flowing current through at least one electrical contact such that when the metal deposit is present in the detection region between the two or more electrical contacts, the metal deposit completes a circuit between the two or more electrical contacts, and when the metal deposit is not present in the detection region between the two or more electrical contacts, there is no complete circuit between the two or more electrical contacts; and measuring an electrical property to detect the presence or absence of the metal deposit in the detection region.

In another aspect of the disclosed embodiments, an apparatus for detecting the presence or absence of a metal deposit on a substrate holder of an electroplating apparatus is provided, including: detection hardware positioned on mounting hardware, where the detection hardware, wherein the mounting hardware comprises a swing arm that swings into place to bring the detection hardware proximate a detection region on the substrate holder, the substrate holder including a bottom and an interior edge, where the detection region on the substrate holder is on the bottom of the substrate holder extending about 5 mm or more from the interior edge of the substrate holder, and where the detection hardware is configured to detect the presence or absence of a metal deposit in the detection region of the substrate holder.

In some cases, the mounting hardware is integral with an electroplating apparatus. Alternatively or in addition, the apparatus for detecting the presence or absence of a metal deposit may be capable of interacting with multiple substrate holders. The mounting hardware may include a swing arm that swings into place to bring the detection hardware proximate the detection region on the substrate holder. Other types of mounting hardware may also be used to rotate, translate, swivel, or otherwise move the detection hardware into place. In some embodiments, the mounting hardware further includes a cleaning assembly for removing metal deposits from the substrate holder. In a particular example, the cleaning assembly includes one or more nozzles configured to shoot a jet of cleaning solution onto the substrate holder.

Many different types of detection hardware may be used. In certain cases, the detection hardware includes a light source and a light detector, where the light source is configured to shine light on the detection region of the substrate holder, and where the light detector is configured to measure light that is reflected off the detection region of the substrate holder. A filter may optionally be positioned between the detection region and the light source, or between the detection region and the detector. The filter may filter out wavelengths of light that are normally reflected by the detection region when no metal deposits are present. In certain cases, the apparatus may further include one or more optical fibers. The optical fibers may be used to carry light between the light source and an optical outlet that shines on the detection region, and/or between an optical inlet positioned proximate the detection region and the light detector. In a particular case, the optical outlet that shines on the detection region and the optical inlet positioned proximate the detection region are provided together as an integrated bundle of optical fibers.

In another embodiment, the detection hardware includes a circular primary excitation coil through which an alternating current flows to thereby generate a changing magnetic field that interacts with the detection region to produce eddy currents. The detection hardware may also include a receiver coil that is distinct from the primary excitation coil, where the receiver coil is configured to measure changes in the magnitude and/or phase of the eddy currents. In a further embodiment, the detection hardware includes two or more electrical contacts that contact the detection region, and an electrical connection between the two or more electrical contacts, such that when a metal deposit is present in the detection region between the two or more electrical contacts, an electrical circuit is complete, but when a metal deposit is not present in the detection region between the two or more electrical contacts, the electrical circuit is incomplete.

These and other features will be described below with reference to the associated drawings.

DETAILED DESCRIPTION

Figure 1:
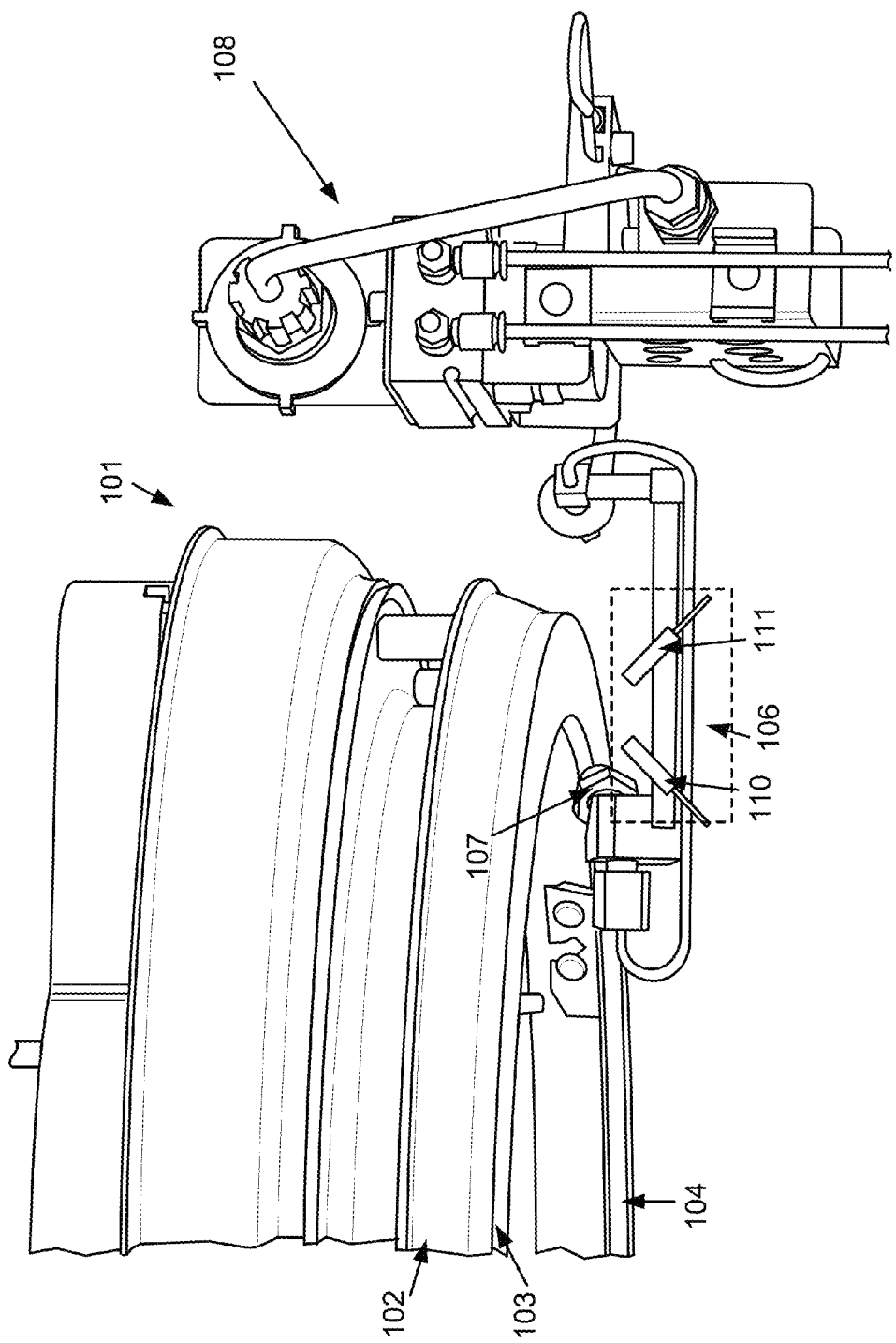
FIG. 1 shows an embodiment of a detection apparatus for detecting the presence of unwanted deposits on the bottom of a cup for holding a substrate during an electrodeposition process.

In this application, the terms "semiconductor wafer," "wafer," "substrate," "wafer substrate," and "partially fabricated integrated circuit" are used interchangeably. One of ordinary skill in the art would understand that the term "partially fabricated integrated circuit" can refer to a silicon wafer during any of many stages of integrated circuit fabrication thereon. A wafer or substrate used in the semiconductor device industry typically has a diameter of 200 mm, or 300 mm, or 450 mm. Further, the terms "electrolyte," "plating bath," "bath," and "plating solution" are used interchangeably. The following detailed description assumes the invention is implemented on a wafer. However, the invention is not so limited. The work piece may be of various shapes, sizes, and materials. In addition to semiconductor wafers, other work pieces that may take advantage of this invention include various articles such as printed circuit boards and the like.

In the following description, numerous specific details are set forth in order to provide a thorough understanding of the presented embodiments. The disclosed embodiments may be practiced without some or all of these specific details. In other instances, well-known process operations have not been described in detail to not unnecessarily obscure the disclosed embodiments. While the disclosed embodiments will be described in conjunction with the specific embodiments, it will be understood that it is not intended to limit the disclosed embodiments.

While the discussion herein focuses on substrate holders constructed with a cup and lip seal, other arrangements may be used. Generally, when the terms "cup bottom" or "substrate holder bottom" are used herein, these terms are intended cover the bottom of any wafer holder, regardless of whether that wafer holder is constructed with a cup as depicted in the figures. The bottom of a wafer holder is generally the side of the holder facing into the electroplating solution. It is typically oriented in substantially the same direction as the face of a substrate being plated, and is often nominally planar to the wafer. Typically, the bottom of the substrate holder is positioned around the peripheral portion of a substrate (such that the substrate holder supports the edges of the substrate), and extends radially outward from the substrate. As used herein, the term lip seal generally refers to a portion of the wafer holder that engages with the edge of the wafer and creates a seal that protects the interior of the wafer holder (including the electrical contacts for connecting to the wafer) from electroplating solution while exposing the entire plating face of the wafer to electroplating solution. Any of a variety of lip seal designs may be used.

For simplicity and clarity, most of the examples herein concern wafer-face-down, "fountain" plating apparatus. In such apparatus, the work piece to be plated (typically a semiconductor wafer or other substrate) generally has a substantially horizontal orientation (which may in some cases vary by a few degrees from true horizontal for some part of, or during the entire plating process) and may be powered to rotate during plating, yielding a generally vertically upward electrolyte convection pattern. Integration of the impinging flow mass from the center to the edge of the wafer, as well as the inherent higher angular velocity of a rotating wafer at its edge relative to its center creates a radially increasing sheering (wafer parallel) flow pattern. Clamshell-type electroplating apparatus having a cup and cone arrangement are frequently used to hold wafers in place before and during electroplating. Examples of clamshell and fountain plating cells/apparatus are included in the Sabre® family of Electroplating Systems produced by and available from Lam Research, Inc. of Fremont, Calif. Additionally, clamshell fountain electroplating systems are described in, e.g., U.S. Pat. No. 6,800,187 filed Aug. 10, 2001 and U.S. Pat. No. 8,308,931 filed Feb. 11, 2010, which are incorporated herein by reference in their entireties. While the description herein focuses primarily on an orientation with the wafer and the holder face down, parallel to the plane of the local earth's surface, it is understood that other orientations, such as angled or normal to the earth surface are not excluded and also envisioned.

Furthermore, while the discussion and examples herein generally focus on the detection of tin/silver buildup, the embodiments may be practiced to detect the presence of any reflective and/or conductive material in the region where the detector is focused. The mechanism for the tin/silver build up process is described in some detail hereafter and elsewhere. As an example of another relevant system, copper plating may build up in the lip seal/cup bottom region during electroplating of copper. The copper deposits may be formed by the creation of partially reduced cupric ions to cuprous ions, or by the creation of organic-additive reducing species at the wafer surface, which may be swept to the wafer edge, lip seal and cup bottom region. These copper deposition routes are shown in the reactions below:

First Example Deposition Route:

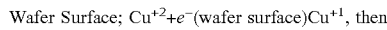
Wafer Surface; $Cu^{+2}+e^-$(wafer surface)$Cu^{+1}$, then

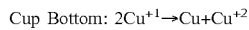
Cup Bottom: $2Cu^{+1} \rightarrow Cu+Cu^{+2}$

Second Example Deposition Route:

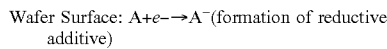
Wafer Surface: $A+e- \rightarrow A^-$(formation of reductive additive)

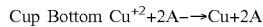
Cup Bottom $Cu^{+2}+2A- \rightarrow Cu+2A$

Problems associated with spurious metal deposits on lip seals and cup bottoms are exacerbated as wafers are designed with more and more features near the edge of wafers, where they are especially likely to be impacted by such plating. Further, the presence of near edge features promotes generation of spurious deposits on wafer holders and seals. The interference between near-edge features and the lip seal plating is much greater when the density of features near the edge is high. The drive towards more near-edge features results from a desire to maximize the number of semiconductor devices that can be obtained from a single wafer.

In the examples presented herein, a plating apparatus includes a cup to support a wafer during plating. The cup holds the wafer in place by supporting the outer periphery of the wafer. The cup therefore has a large opening in its center, the opening having a slightly smaller diameter than the diameter of the wafer. FIG. 1 shows an example of a cup 102 having cup bottom 103 in the context of a wafer positioning system 101. In certain cases, the cup 102 and/or cup bottom 103 may be coated with a material having non-sticking characteristics, such as polyvinlyidene fluoride (PVDF, e.g., Kynar® from Arkema of Colombes, France) or polytetrafluorethleyene (PTFE, e.g., Teflon® from Dupont of Wilmington, Del.), silicones, or silicon and oxygen glass-like ceramic non-stick materials such as Cuisinart's "Ceramica™" or Thermolon™.

The cup 102 generally has a short (e.g., about 1.0-1.5 mm tall) vertical inner wall. A thin (e.g. 0.75 to 1.5 mm) lip seal 104 is positioned at the top of this vertical inner wall, and engages with the wafer during plating, which forms a peripheral seal. During electroplating, the lip seal 104 protects electrical contacts (not shown) which are located radially outside of the lip seal 104. At the bottom of the cup's inner vertical wall, the cup extends horizontally radially outward (radially outwards and parallel to the wafer). This horizontal surface is the cup bottom 103.

While undesired plating on the cup itself initially begins on the cup's inner vertical surface where the cup 102 meets the lip seal 104, the plating can progress down this vertical inner wall surface, around the corner of the cup 102, and radially outward on the cup bottom 103. When the plating reaches the cup bottom 103, significant manufacturing defects can occur, and wafers that are processed while there is plating on the cup bottom 103 are often ruined or have very low yields. The transition to cup bottom plating and growth is due in part to the fact that the metal more easily adheres onto the cup 102 (especially the cup bottom 103) as compared to the lip seal 104. Although the cup bottom 103 and other parts of the cup 102 may be coated with non-stick coatings such as a fluorinated polymer coating (e.g., polytetrafluoroethylene, PTFE) to help discourage metal from attaching to this surface, deposits can still form on the cup bottom 103 from time to time. In many cases, once plating starts to occur on the cup bottom 103, the rate of deposition substantially increases and the deposition can quickly become out of control and plate the entire cup bottom 103. In addition to the wafer positioning system 101, FIG. 1 shows hardware related to optical cup bottom plating detection. This hardware is discussed further below.

Because tin-silver alloys are often deposited toward the end of semiconductor manufacturing processes (for example, as tin-silver solder contacts), the wafers used in the tin-silver deposition process are typically very expensive, having been through many processing operations before they reach this point in the overall production process. Therefore, the failure to detect plating on the cup bottom and potentially creating wafers that are low yield or out of specification can be especially costly.

Without being limited to a particular theory, it is believed that spurious deposition of tin-silver alloy occurs as a result, at least in part, of the significantly differing reduction potentials of atomic tin versus atomic silver, and furthermore, that growth of spurious deposits occurs first by the plating of tin (with little silver content) at the lip seal wafer interface, and the film grows via a displacement reaction $(Sn+2Ag^+ \rightarrow Sn^{2+}+2Ag)$ on the surface of the lip seal and cup bottom, resulting in a substitution of two silver atoms (having oxidation state +1) for every atom of tin (having oxidation state +2) and a corresponding growth in the volume of the spurious film. Once again, without being limited to a particular theory, it is believed that other metal or alloy deposits formed from metals having significantly different reduction potential, for example, having a reduction potential difference greater than about 100 mV or more, may lead to the same or similar problems involving spurious metallic deposition on the lip seal and cup bottom of an electroplating assembly.

Metal deposits on the cup bottom can lead to both (1) local non-uniformities in the region near the cup bottom deposit due to local variations in current and potential distribution, as well as (2) a decrease in the average thickness of the deposit over the entire wafer. The loss of yield therefore is not only related to the generation of stray metallic particles, but also due to the scavenging or "current sinking" of charge intended for plating on the wafer itself. The first impact is generally local to the region on the wafer around where the cup bottom plating has occurred, as locally, current is drawn away from the features near the edge of the substrate to the cup bottom, making features in that edge vicinity thinner than desired. With increasing extent of cup bottom plating, the second impact (thinner than desired average plating thickness over the entire wafer) occurs as the total amount of current plated on the cup bottom becomes significant relative to the total amount of current needed to plate the entire wafer, and therefore, the average thickness of the features plated on the wafer drops below a target average thickness.

Substrates that have lower amounts of open area (areas where electroplating is desired) are more sensitive to the presence of cup bottom plating than substrates that have higher amounts of open area. These low open area/low feature density substrates are more sensitive due to the fact that the ratio of cup bottom plating area to desired substrate plating area is relatively high. In other words, because the area in which current should be delivered to the substrate is small, it is easy to redirect a substantial amount of this current when cup bottom plating is present. In contrast, for high open area/high feature density substrates, the area where current is desired to be delivered is larger. As such, the initiation of cup bottom plating will draw off a relatively smaller portion of the current delivered to the wafer. But in both cases, it is important to immediately detect small amount of plating as quickly as possible to avoid processing wafers that do not plate with the target uniformity of average thickness.

In both plating problems listed above, the harmful effects occur because the metal deposit effectively scavenges current from the surface of the wafer (where it is desired) and redirects it to the metal deposit itself (where it undesirably causes even more plating to occur at the site of the deposit). In many tin/silver deposition processes such as the formation of the relatively low I/O count bumps on memory devices, the amount of open area on the wafer (i.e., the area where current is intended to be directed and where plating occurs) can be very small (e.g., about 0.5-3% of the face of the wafer). Therefore, the current is directed to a fairly small area on wafer, which may be comparable to size of a metallic deposit on the cup bottom. In part because these two areas are comparable in size, a proportionately large amount of the current that should be directed to the open areas on the wafer is instead directed to the cup bottom. Thus, the formation of even a small amount of plating on the cup bottom can significantly impact the wafer's plating around that feature, and if the deposit is sufficiently large, it can impact the overall plated thickness of the wafer. Of course, this can cause failure of many or all dies on a wafer. The area of the cup bottom surface for a 300 mm wafer holder may be typically approximately 200 cm$^2$. The exposed area of a 300 mm wafer is about 700 cm$^2$, and if that 300 mm wafer is masked to expose a small portion, e.g., 1%, of the wafer surface, one will be plating an area of about 7 cm$^2$. If a very small portion of the cup bottom, for example if only about 0.5% of the cup bottom, or about a 1×1 cm segment (1 cm$^2$) ends up plated, the average rate of plating on wafer could decrease by a substantial amount, for example by about $\frac{1}{7} \times 100 = 14\%$.

Because spurious tin/silver buildup can lead to the outlined problems, it is important that tin/silver deposits be detected and then removed or cleaned away from the lip seal and cup bottom, or the cup bottom and lip seal be replaced. Different cleaning techniques may be used to remove the unwanted deposits. In some cases, the cleaning may be done on an automated basis. In other cases, cleaning may be initiated and/or performed manually. Example techniques for cleaning a substrate holder are further discussed and described in the following U.S. Patent Applications, each of which is incorporated by reference herein in its entirety: U.S. patent application Ser. No. 13/563,619, filed Jul. 31, 2012, and titled "AUTOMATED CLEANING OF WAFER PLATING ASSEMBLY"; U.S. patent application Ser. No. 13/853,935, filed Mar. 29, 2013, and titled "CLEANING ELECTROPLATING SUBSTRATE HOLDERS USING REVERSE CURRENT DEPLATING"; and U.S. patent application Ser. No. 13/852,767, filed Mar. 28, 2013, and titled "METHODS AND APPARATUSES FOR CLEANING ELECTROPLATING SUBSTRATE HOLDERS."

In some embodiments, the cleaning technique involves shooting a jet of cleaning fluid (e.g., deionized water, though other cleaning fluids may be used as discussed below) in the direction of the lip seal and/or cup bottom. The cleaning fluid removes the tin/silver buildup as the clamshell and cleaning fluid jet rotate with respect to one another.

Various different cleaning agents/fluids may be used. In some embodiments, selection of the cleaning agent will depend on the composition of the unwanted deposits to be removed. For instance, removal of unwanted tin-silver alloy deposits may successfully employ an oxidizing acid solution into which both tin and silver metal and salts are oxidizable and/or soluble. Thus, in some embodiments, the cleaning agent may include an acid and/or oxidizing agent. A particular example of an appropriate cleaning agent or cleaning solution for removing tin-silver alloy deposits is a solution of nitric acid. Such a solution may have, for example, a nitric acid concentration of about or greater than 5%, 10%, 15%, 20%, 25%, 35%, or 50% by weight; or about or less than any one of these concentrations; or within a range defined by any pair of these concentrations. In some embodiments, a cleaning agent/solution may employ multiple acids, such as, for instance, a combination of nitric acid and hydrochloric acid (i.e., to form aqua regia) with both acids present in any of the above recited concentrations or within the above recited ranges of concentrations. However, other acids and combinations of acids may also be employed—again, in any of the above recited concentrations or recited ranges of concentrations. In some embodiments, the cleaning agent may be a metal complexing agent, and typically a complexing agent selected for its ability to complex a metal making up the deposits to be removed. For instance, a complexing agent selected as a cleaning agent may be oxalate ion since it complexes tin. In some embodiments, a silver complexing agent may be selected as a cleaning agent, such as various mercapto-derivative compounds.

Unfortunately, the cleaning process may not always be 100% effective, and tin/silver material may remain on the electroplating apparatus after cleaning. Where jets of cleaning fluid are used to remove unwanted deposits, for example, the jets are typically aimed at the inner vertical region of the wafer holder (particularly the lip seal region and the cup inner vertical wall surface). Because the tin/silver material is particularly adherent to the less flexible inner vertical wall surface and cup bottom (where it may become "anchored" due to the propensity of tin), it is not unusual for some tin/silver material to remain on the inner wall surface after autocleaning. Significant work has been undertaken to make this process highly efficient and effective. As tin-silver particles grow on the lip and vertical wall surface with wafer processing, they become more susceptible to the forces of the water jet autocleaning process and are removed (current data shows a removal efficiency of about 99.98% under normal production operating conditions). Unfortunately, the process is not 100% efficient, so about 1 time in 5,000-10,000 processed wafers, the cleaning process may fail. Further, in certain cases, the autocleaning process experiences a hardware or process glitch such that the autocleaning is unsuccessful. For example, the cleaning jet may be misaligned, the arm on the hardware may swing in but be physically broken, the pressure of the cleaning jet may be too low, etc.

Once plating occurs on the cup bottom, the deposit often cannot be removed by an autoclean process, and must instead be removed through a different process such as dipping or manual swiping chemical etching (e.g., using a chemical solution mixture of concentrated nitric acid with or without hydrogen chloride to manually remove the deposits). While there may be certain checks in place to ensure that autocleaning takes place (e.g., a check to ensure that the autocleaning arm moves into position and a sensor to ensure adequate flow and/or pressure), prior autocleaning systems have not included any mechanism for detecting whether the cleaning process has been successful. Therefore, various cleaning defects may go unobserved, leading to poor quality plating of subsequent wafers. A technique of confirming that there is no cup bottom plating before processing high valued wafers is highly desirable.

The issues described herein may also be encountered with other types of cleaning techniques. One alternative cleaning method includes rotating a cleaning disc that has cleaning fluid therein, where the rotation results in the cleaning fluid emanating from peripheral pores in the disc. The cleaning solution then contacts the substrate holder to remove the unwanted deposits. In some embodiments, the disc may have a substantially circular upper surface, a substantially circular lower surface, a substantially circular edge joining the upper and lower surfaces, and a plurality of pores opening at the edge. The disc may also have an interior region extending into the interior of the disc. In some embodiments, the pores are dimensioned such that the cleaning agent is retained in the interior of the pores by an adhesive force between the cleaning agent and the interior surface of the pores. One method of using such a cleaning disc may involve loading a cleaning agent into a plurality of pores of the cleaning disc, positioning the cleaning disc within a semiconductor processing apparatus, and rotating the disc or otherwise manipulating the disc to release cleaning agent from the plurality of pores such that elements of the apparatus are contacted by the released cleaning agent. This cleaning technique and apparatus therefore are further described in U.S. patent application Ser. No. 13/563,619, which was incorporated by reference above.

Another alternative autocleaning technique involves reverse current deplating. Such cleaning involves positioning a cleaning (deplating) disc in an electroplating cup similar to a regular processed substrate. The front surface of the cleaning disc includes a corrosion resistant conductive material to form electrical connections to deposits on the cup's surfaces. The disc is sealed in the cup and submerged into a plating solution. A reverse current (i.e., a current that is opposite that typically used to plate material on a substrate) is then applied to the front conductive surface of the disc to initiate deplating of the deposits. Sealing compression in the cup may change during cleaning to cause different deformation of the lip seal and to form new electrical connections to the deposits. This cleaning technique is further described in U.S. application Ser. No. 13/853,935, which was incorporated by reference above.

Before autocleaning was implemented, cleaning generally took place manually. An operator would use a swab dipped in concentrated nitric acid solution or other reagent capable of dissolving metal to remove the metal buildup. The operator was able to visually inspect the lip seal and cup bottom to ensure complete removal of the metal. Of course, this was a time consuming and inefficient process, which could be hazardous to the operator. Autocleaning eliminated these problems and represents a significant advance over the prior manual techniques. However, with the implementation of autocleaning, there is no operator to visually inspect for buildup regularly, and wafers may continue to be processed even after cup bottom plating occurs, leading to the loss of these valuable wafers. Although an operator may periodically come in to inspect the plating apparatus, the operator has a limited ability to check for buildup due to time constraints and other various factors. Thus, a visual inspection may only occur once or twice per day, for example. By the time a visual inspection occurs, many valuable wafers may have already been processed under cup-bottom-plated conditions, resulting in the loss (or low yield) of these expensive wafers. In light of this difficulty, a method and apparatus for detecting whether a cup bottom of a plating apparatus has residual metal deposited thereon would be useful. Such method and apparatus could be deployed at a frequency as high as every wafer processed.

Methods of Detecting Residual Metal Deposits on Cup Bottom

Certain embodiments herein provide methods of detecting whether and to what degree residual metal deposits are present on a cup bottom. These methods may be practiced at the same time as, or immediately following, a cleaning operation, though they may be performed at any time when plating is not occurring. In certain cases the detection methods are practiced each time an autocleaning process occurs. In other cases the detection methods are practiced more or less frequently. For example, detection may occur after each wafer is processed, after a certain number of wafers are processed, after a certain amount of charge (measured in coulombs, for example) has been transferred during electrodeposition processes, or after a certain total amount or thickness of film has been deposited during electrodeposition processes.

The detector is usually designed to detect deposits on the cup bottom, near the vertical inner wall. For example, the detector may detect deposits on the cup bottom within about 20 mm of the vertical inner wall, or within about 10 mm, or within about 5 mm. It is beneficial to detect metal deposits in this region for several reasons. First, once metal begins plating on the cup bottom, it can rapidly grow out of control due to the mechanisms described above. Thus, it is desirable to detect deposits on the cup bottom very close to the wafer edge, where the deposit first extends beyond the point where autocleaning is effective. In this way, the problem of cup bottom plating may be detected and remedied before it gets out of control.

A loose analogy is the removal of a pre-cancerous skin lesion and the formation of a cancerous skin tumor. Suspected lesions (analogy to lip seal plating particles) are periodically removed as pre-cancerous lesions. However, if some are missed, they may grow into a much less controllable (and potentially dangerous) cancerous lesion (analogy to cup bottom plating). The autoclean process is intended to remove the lip seal particles (pre-cancerous lesions), and the autodetect hardware determines the presence of cup bottom plating (cancerous lesions), that would require a more extensive intervention.

While it would be possible to detect deposits on the lip seal itself, such detection would only be of limited value, since the autocleaning techniques are performed fairly frequently to remove these lip seal deposits. Metal deposits frequently occur on the lip seal region, and must form there prior to initiating cup bottom plating (though oftentimes the lip seal deposits are removed and the cup bottom plating does not occur). Autoclean hardware and processing are designed to remove the material from the lip seal and inner vertical wall of the substrate holder/cup before they grow and reach the cup bottom. It has been established that a few residual lip seal and inner-wall deposits do not necessarily cause significant deposition problems on the wafer between the time that they are first formed and the time they are eventually removed. For example, in some cases a small amount of metal will deposit on the lip seal region and remain there as several wafers are processed, possibly growing somewhat bigger each time. Eventually the autoclean process is deployed, and the deposit is removed before it reaches the cup bottom. In some cases removal of deposits at the lip seal is facilitated due to the flexure of the elastomeric lip seal or the size of the particle itself. Because autoclean generally keeps lip seal deposits in check, and a non-zero signal is not expected in the lip seal region, and because plating in this region is not fatal, the disclosed detection embodiments focus on detecting metal deposits on the cup bottom, rather than the lip seal region. Metal detection in the cup bottom region provides a much more useful indication of problematic plating conditions.

Any of various detection methods may be used to determine whether the cup bottom is sufficiently clean to continue processing wafers. Typically the methods are sensitive to the presence of a thin layer of metal on a conductive or non-conductive surface. In one embodiment, an optical detection method is used. In another embodiment, an eddy current method is used. In an additional embodiment, a rolling resistance method is used.

One technique for implementing an optical detection method includes shining a source light on the detection region of the cup bottom and measuring the amount of light that is reflected. This technique is performed while the wafer holder and/or detector is rotated. Metal deposits may exist at only one or a few azimuthal positions on the wafer holder bottom. Returning to the embodiment of FIG. 1, optical detection hardware 106 may be positioned on a swing arm actuated apparatus 108. The optical detection hardware 106 may include two principal components: a light source 110 and a detector 111. The swing arm 108 may also include a nozzle 107 for providing a jet of cleaning fluid used to remove deposits from the cup bottom 103. Where other cleaning methods are used, the nozzle 107 may be absent from the swing arm 108.

In one method of performing the detection, a broad spectrum (e.g., white) light source is used with a black or colored cup bottom. The black or colored cup bottom will absorb some or all wavelengths of the white light, and the background reflected signal will be quite small. However, if there is metal on the surface, the metal will reflect a significant amount of the light from the light source, and the reflected light will be detected by the detector.

In some implementations, the source light is colored and the cup bottom is colored complementary to the color of the light source (e.g., a red light source and a green cup bottom). By using complementary colors, the background signal is minimized because light at the frequency of the source is absorbed by the colored cup bottom, and a reflected signal, if present, is most easily detected. The complementary colored cup bottom absorbs most of the light from the light source except where a deposit is present to reflect the incident light. The color of the incident light may also be selected to differentiate from the color of the metal deposit over the cup bottom (e.g., using a blue, green, or blue-green cup to detect copper deposits).

Where a colored cup bottom is used, the color may result from a cup-bottom-coating. In certain embodiments, the coating is made from a fluorinated polymer (e.g., PTFE and/or PVDF) to help discourage deposits from forming on the cup bottom. The coating may also contain colored pigment.

In certain embodiments, light from a white light source is filtered by having a filter positioned between the cup bottom and the detector (or between the light source and the cup bottom) to filter out certain wavelengths from the reflected (or incident) signal. The optical filter may be tuned to block light of the reflection spectra that is the same color as the cup bottom. For example, where a green cup bottom is used, a filter may be used to block green light between the cup bottom and the detector (or between the cup bottom and the light source). Thus, the filter minimizes background signal that is reflected off the cup bottom itself and thereby improves the sensitivity of the detector. In some cases, the detector itself may be relatively insensitive to light of the color of the chosen cup bottom design.

Whatever method is being used, it is important to have a strong differential between (a) a signal received at the detector when the light is being reflected off a deposit, and (b) a signal received at the detector when no deposit is present.

Other detection techniques may also be used. In certain implementations, an eddy current method is used. Eddy current testing uses electromagnetic induction to detect the presence of (or flaws in) conductive materials. A circular coil carrying current is placed near the test object (in this case a cup bottom), and an alternating current in the coil generates a changing magnetic field that interacts with the electrically conductive portions of the test object to produce eddy currents. Variations in the magnitude and phase of the eddy currents (or merely the presence of such currents) may be monitored, such variations corresponding to changes in electrical conductivity or magnetic permeability of the test object (for example, due to the presence of a metal deposit on a plastic cup bottom), or the presence of flaws therein. The variations may be monitored by using a second receiver coil or by measuring changes to the current flowing in the primary excitation coil.

The eddy current technique may not be appropriate in all applications. For example, the technique is not very sensitive to the difference between metal which is undesirably plated on a cup bottom and metal that is inherently part of the cup (or other metal which is present in this region). For example, if the cup bottom consists of a metal element having a dielectric coating, detection of the cup bottom plated metal may prove difficult. In certain implementations, the cup bottom includes a metallic structure, such as a metallic reinforcing bottom, to help provide structural stability. In these cases, eddy current detection should be avoided. However, where the cup does not contain metal, the eddy current detection method may be used.

In certain additional embodiments, a rolling or moving resistance measurement method is used to detect the presence of metal deposits. In this method, there are two or more contacts that move around the surface of the cup bottom. A set of two (or more, for example four where a four point measurement technique is used) electrical brushes or rollers swipe or roll across the cup bottom surface, and the resistance between the brushes or rollers is measured. The resistance to the passage of current between the two or more cup bottom electrical contact elements will decrease if measuring at a cup bottom position where a metal deposit is present. A resistance meter can be used for this detection. In some embodiments, a voltage may be applied across the contacts, and a detector may be configured to look for a threshold current to be established between the contacts.

Where no metal deposit is present, there is no complete electrical connection between the contacts and a high resistance or no current will pass. However, where metal is present, it serves to provide electrical connection between the contacts, thereby completing a circuit and establishing a measurable current or resistance. Generally, the contacts should be brushes or rollers, as opposed to needles. Capacitive sensors, sensitive to the environmental capacitance around the probe may similarly be useful if the construction of the cup bottom and its environment enable a differential signal between cases where no cup bottom plating is present and cases where cup bottom plating has occurred. The thickness of cup bottom plating may be between about 5-10 µm, in certain cases.

Because it is advantageous to monitor for deposition around the entire cup bottom, the detector and cup bottom may be designed to rotate or scan with respect to one another. Further, because the cup bottom in the particular embodiment discussed in detail here is typically rotatable, it is not necessary for the detector itself to rotate. However, in certain implementations, the detector may be rotated and/or otherwise moved (e.g., translated with respect to the cup bottom). In some embodiments, the speed of rotation during detection is between about 1-500 RPM, for example between about 30-150 RPM. In cases where the cup bottom is not part of a plating module rotating fixture and the wafer moves to the plating station (e.g., a tool configuration where the wafer holder is moved inside a plating tool to a plating station), a mechanism for scanning along the edge of the cup bottom would be separately required. Any hardware that allows the detector to scan the edge of the cup bottom may be used.

Figure 2:
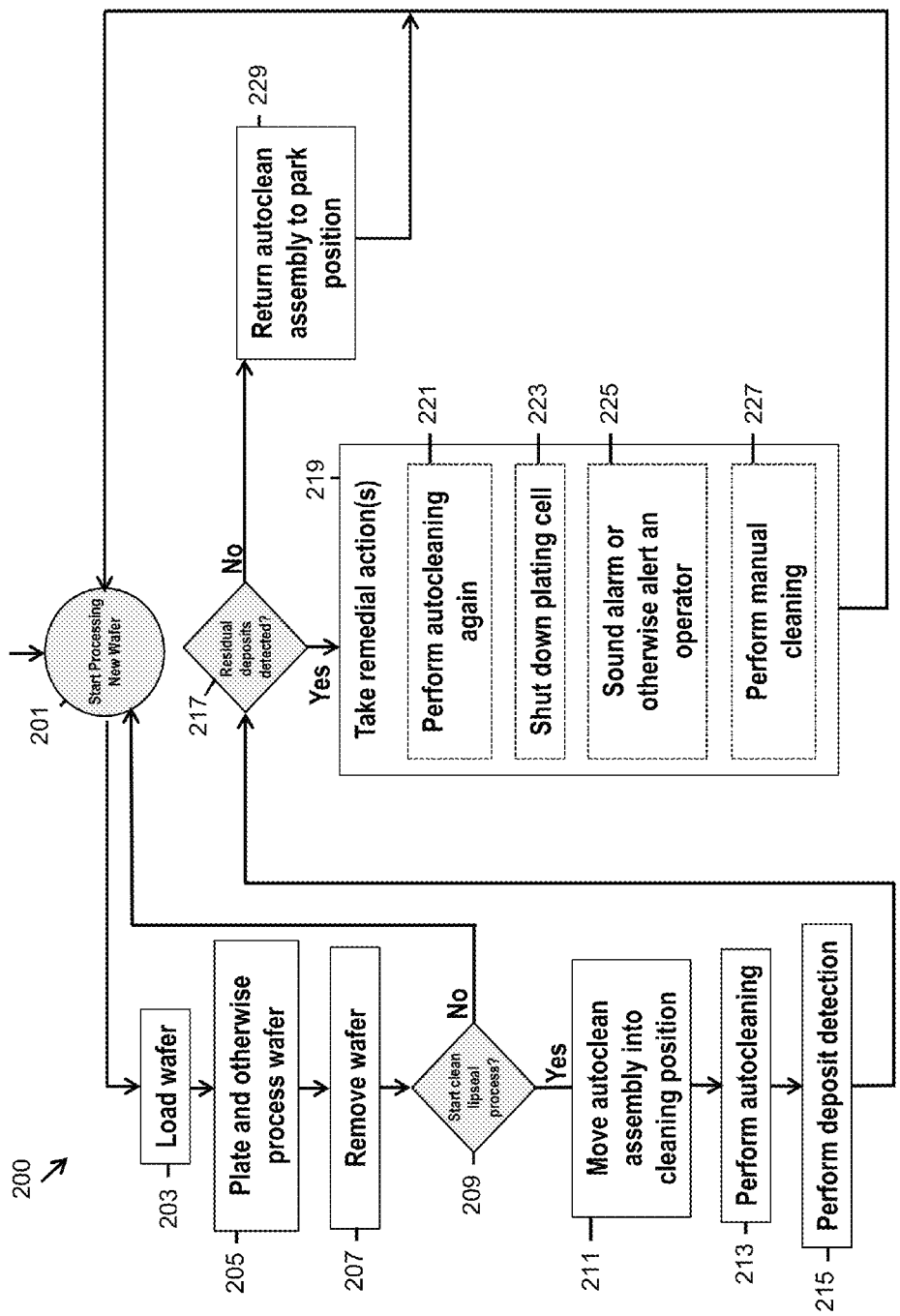
FIG. 2 presents a flowchart for a method of processing wafers, cleaning an electrodeposition substrate holder, and detecting the presence of unwanted deposits on the bottom of a substrate holder.

FIG. 2 shows a flowchart for a method in accordance with the embodiments herein. The process 200 starts at block 201 where processing a new wafer begins. As illustrated at block 203, a wafer is loaded into the electroplating apparatus. At block 205, the wafer is plated and/or otherwise processed. At block 207, the wafer is removed from the substrate holder. Next, at block 209 a lip seal cleaning process may or may not be scheduled. If the lip seal cleaning process is not undertaken, a new wafer may begin to be processed at block 201. If the lip seal cleaning process is scheduled/undertaken, however, the process 200 will continue in block 211, where the autoclean assembly is moved into the cleaning position. The autoclean process is performed at block 213. Next, at block 215 deposit detection is performed. If no residual deposits are detected at block 215/217, the autoclean assembly may be returned to its park position in block 229, and a new wafer may begin to be processed at block 201. By positioning the autoclean assembly in the park position, it ensures that the assembly will not interfere with processing of subsequent substrates. If residual deposits are detected at block 215/217, some remedial action is undertaken in block 219 before a new wafer begins to be processed at block 201. The remedial action may include, for example, performing autocleaning again 221, shutting down the plating cell (i.e., taking the plating cell offline) 223, sounding an alarm or otherwise alerting an operator 225, or performing manual cleaning 227. One or more of these remedial actions may be undertaken when residual deposits are present after autocleaning. Optionally, the deposit detection may be performed again after the remedial action is undertaken to ensure the cup bottom is sufficiently clean before plating additional wafers.

While the embodiment shown in FIG. 2 shows a typical process flow, many of the elements related in this flowchart are not necessary to practice the embodiments herein. For example, the detection can occur at any time that plating is not taking place, and does not need to follow a plating or autocleaning procedure. Additionally, the wafer need not be removed before detection takes place if the autocleaning process is not undertaken, or if the cleaning process employed does not require removal of the wafer. In other words, detection can be performed in the electroplating cell.

As shown in FIG. 2, a variety of remedial actions may be taken where residual deposits are detected. For example, where deposits remain on the cup bottom, an alarm may sound to notify an operator that the plating cell is dirty. The operator may then choose to undertake additional action to clean the cup bottom. In one case, the autoclean process may be repeated. However, because the tin/silver material may be anchored to the cup bottom surface, an additional autoclean may not be sufficient to remove the deposit from the cup bottom. Manual cleaning may also be performed to remove deposits on the cup bottom. In any case, plating should not continue in the cup bottom plated electroplating apparatus until the deposit is removed. Otherwise, plating additional wafers in the dirty electroplating apparatus could result in non-usable or low yield substrates. If the cup bottom plated apparatus cannot be cleaned right away, it may be taken offline to avoid damaging subsequent wafers. An additional flowchart that describes an electrodeposition and autocleaning process can be found in FIG. 7 of U.S. patent application Ser. No. 13/852,767, which was incorporated by reference above. The corresponding description provides additional details on how these processes may be undertaken in certain embodiments.

Detection Apparatus

In one embodiment, an electroplating apparatus includes a detection mechanism that is incorporated into the apparatus. The electroplating apparatus includes a cup for holding a wafer during plating, a lip seal to help seal the interface between the wafer and cup, electrical contacts to apply current/potential to the wafer during plating, and other conventional electroplating apparatus components (e.g., an electroplating chamber having inlets and outlets, etc.). The detection mechanism may be positioned on an arm that swings into place during the time between processing different wafers. Further, the detection mechanism may be incorporated directly on an autocleaning assembly (which itself may or may not be incorporated into an electroplating apparatus). This embodiment is advantageous because both the detection mechanism and the autoclean mechanism may be placed on a single swing arm that moves into place when needed, as shown in FIG. 1. Having a single swing arm is beneficial because it makes the apparatus more compact, easier to use, and less expensive to manufacture. Further, a single swing arm may be advantageous because it results in fewer potential failure points compared to cases where multiple swing arms are used. In another embodiment, the detection mechanism may be a standalone instrument, which may be installed in an autoclean station, a plating cell, or some other location dedicated to detection. This standalone embodiment may be beneficial because a single detection mechanism may easily be shared by wafer holders in many electroplating cells.

The detection mechanism is positioned such that when it is engaged, it detects deposits on the cup bottom within about 20 mm of the cup's vertical inner wall, or within about 10 mm, or within about 5 mm of this wall. In some cases the detection mechanism may be mounted on a fluid supply line which supplies fluid to the autocleaning nozzle. The detection mechanism may be removable, or it may be permanently attached to the autocleaning assembly or electroplating mechanism. If the detection mechanism is permanently attached to another element, there should be a way to move the detection mechanism out of the way during plating (e.g., the detection mechanism may be permanently affixed to an arm that swings into place). The detection mechanism should be mounted in a relatively stable manner in order to maintain proper alignment of the detector (e.g., alignment between a light source and a light receiver where an optical reflective intensity detector is used).

Various implementations of optical detection methods are available. In one case, a light source and a light detector are separately positioned near the cup bottom to detect deposits thereon. This embodiment is shown in FIG. 1, with light source 110 and detector 111. In such designs, the light source and light detector are located so that they are at the same but opposite angles from the normal to the cup bottom (i.e., the angle of incidence equals the angle of reflection) and in the same plane. In another implementation, light from the source and/or light to the detector travels through an optical fiber or other waveguide. One can consider the light source's or the light detector's location and angle in this case as being relative to the cup, as the ends of the optical fiber are in the vicinity of the cup bottom.

In some designs, the incident and reflected light travel through free space. In some designs the light travels through a layer of water between the ends of the optical fiber and the cup bottom surface. In optical fiber designs, the source and detector can be positioned with greater freedom. In other words, the source and detector themselves need not be offset by the same angle from the normal, and need not be in the same plane. However, the ends of the optical fiber (e.g., the end of the fiber from which light emanates from the light source, and the end at which reflected light enters the fiber connected with the detector) still need to be carefully positioned. As used herein (unless otherwise specified) a light source can include one or more optical fibers from which light is emitted toward a cup bottom, and a light receiver can include one or more optical fibers into which reflected light enters, and which is connected with a light detector. Each optical fiber has an optical inlet and outlet. The outlet of the source light fiber and the inlet of the light receiving fiber should be positioned near the substrate holder. A particularly useful compact design is one in which the light source and light receiver are in very close proximity at their ends. In one example, the light source and/or light receiver are formed by a large number of fibers (e.g., at least about 10, or at least about 50 fibers in some cases), which may be bundled together, and which are positioned near the cup bottom. In some embodiments, a light source made of a bundle of optical fibers points source light directly at (i.e., normal to) the cup bottom. In some embodiments, the fibers are substantially coaxially arranged over some distance. The source light may be delivered by some or all of the fibers in the bundle. In certain cases, other fibers in the bundle may be used to receive reflected light and transmit it to the detector. In one implementation, about half of the fibers provide light from a remote light source and about half of the fibers receive light reflected off the cup bottom and carry the reflected light to the detector. Other ratios of numbers of fibers for delivering the probe light and collecting the reflected light can be used.

Figure 3B:
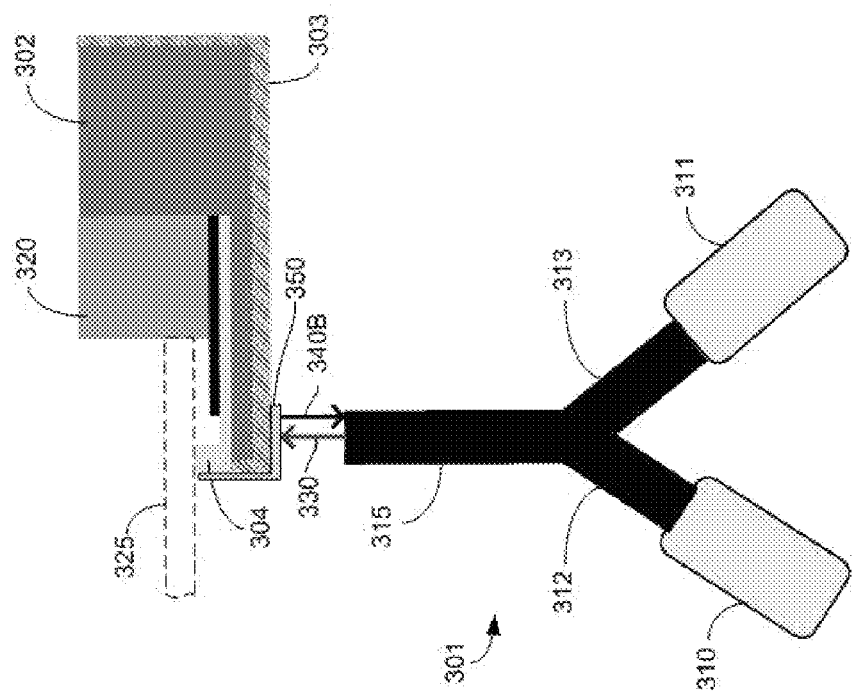
FIGS. 3A and 3B depict optical detection hardware including a bundle of optical fibers for detecting the presence of unwanted deposits on the bottom of a substrate holder.
Figure 3A:
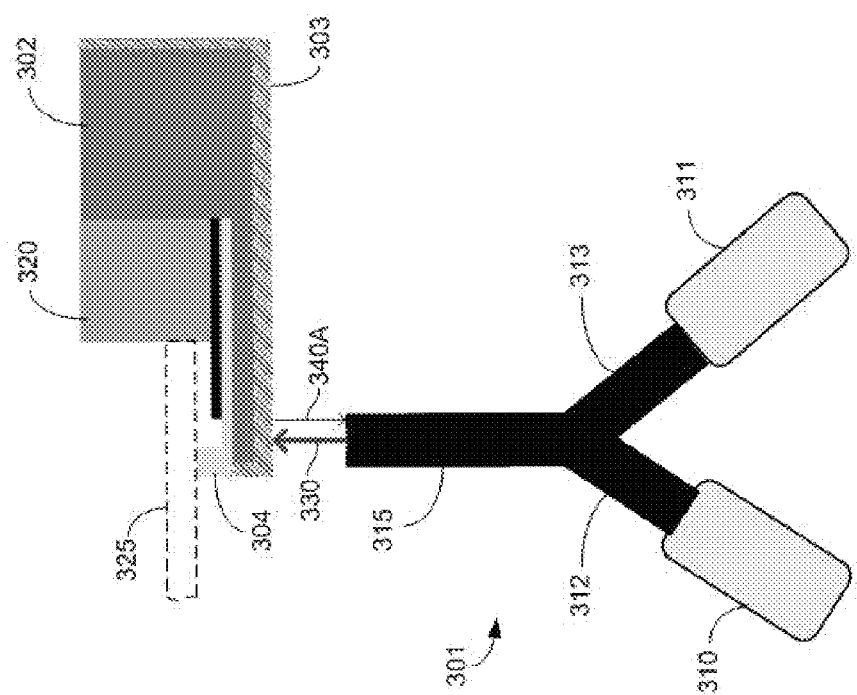

FIGS. 3A and 3B depict light detection hardware 301 interacting with a substrate holder including a cup 302 with cup bottom 303, lip seal 304, and an electrical contact buss cylinder 320. The electrical contact buss cylinder 320 may be integral with the cup 302 in some embodiments. When used for electroplating, a substrate is placed in the substrate holder at location 325, shown in a dotted box. The substrate may or may not be present at location 325 when detection takes place. The optical detection hardware 301 includes light source 310 and optical detector 311, as well as optical fibers 312 and 313, which combine to form optical fiber bundle 315. The optical fibers shown at 312 carry light from the light source 310 and shine on the cup bottom 303 from bundle 315. The incident light being emitted from optical fibers 312/315 is shown by the arrow 330. The optical fibers shown at 313 carry light that has reflected off the cup bottom surface 303 to the detector 311. Light that reflects off of the cup bottom 303 is shown by the arrows 340A and 340B. In FIG. 3A, no metal deposits are present on the portion of the cup bottom surface 303 that is being evaluated. As such, there is very little light 340A reflected back toward the bundle 315. The relative thinness of arrow 340A is intended to convey that relatively little light is being reflected back. In contrast, in FIG. 3B, a metal deposit 350 is present on the cup bottom (and on the vertical inner wall/lip seal 304 region). Therefore, a much greater portion of the incident light 330 is reflected back at 340B. The relative thickness of arrow 340B, as compared to 340A, is intended to convey that a greater portion of the incident light 330 is reflected back toward the bundle 315.

Typically, the detector is a device that can measure optical reflected light intensity. Examples of such devices include photodetectors such as semiconductor photodiodes, photomultiplier tubes, etc. Regardless of the type of device chosen, the installed device measures the intensity of light that enters the detector after being reflected off of a surface/object. The detector may measure the reflected light's intensity over a broad or narrow band of wavelengths. The detector and associated optics are designed such that it can differentiate between (a) a signal received when the light is being reflected off a deposit, and (b) a signal received when no deposit is present.

Certain adaptations are possible to increase the sensitivity or discriminating power of the detector. For example, the light from the light source may be colored such that the light is substantially absorbed by a clean cup bottom and/or reflected by a metallic deposit. Thus, in certain embodiments, the color of the cup bottom may be complementary to the color of the source light. In certain embodiments, a filter is used to block certain wavelengths of light, particularly wavelengths normally reflected (or not absorbed) by the cup bottom. These adaptations are further discussed above.

In some implementations, the detector is an eddy current sensor. The eddy current sensor may include a primary excitation coil which receives an alternating current from a driver. The alternating current creates a changing magnetic field which induces eddy currents in the target material. In certain cases, the eddy currents are monitored through the use of a second receiver coil. Alternatively or in addition, the eddy currents may be monitored by measuring changes to the current flowing in the primary excitation coil. Where an eddy current detector is used, the detector and the cup bottom should be maintained at a uniform distance during detection, as this technique is quite sensitive to changes in distance.

The detector may also be a rolling resistance detector. This type of detector includes two electrical contacts that touch the test surface (e.g., the cup bottom), an electrical connection between the two contacts, and a power source. The two contacts are positioned such that they contact the cup bottom with a small distance between the contacts (e.g, the contacts may be about 0.25-4 mm apart on the cup bottom). Where no deposit is present, the circuit between the contacts is incomplete and no signal is generated. Where a deposit is present, the metal deposit completes a circuit between the two contacts and a detectable signal is produced. In some cases the contacts may be rollers, while in other cases the contacts may be brushes.

Other types of detectors may also be used within the scope of the present disclosure. Examples include capacitive or magnetic sensors. Magnetic sensors may be appropriate when the materials involved are permanently magnetic or are susceptible to magnetic forces (e.g., Fe, Ni, Co).

Many apparatus configurations may be used in accordance with the embodiments described herein. One example of a wafer holder includes a clamshell fixture as mentioned above that seals a wafer's backside away from the plating solution while allowing plating to proceed on the wafer's face. The clamshell fixture may support the wafer, for example, via a seal placed over the bevel of the wafer, or by means such as a mechanical force applied to the back of a wafer in conjunction with seals applied near the bevel. A "cone" is sometimes employed to provide the mechanical force.

Electroplating Systems

Figure 4:
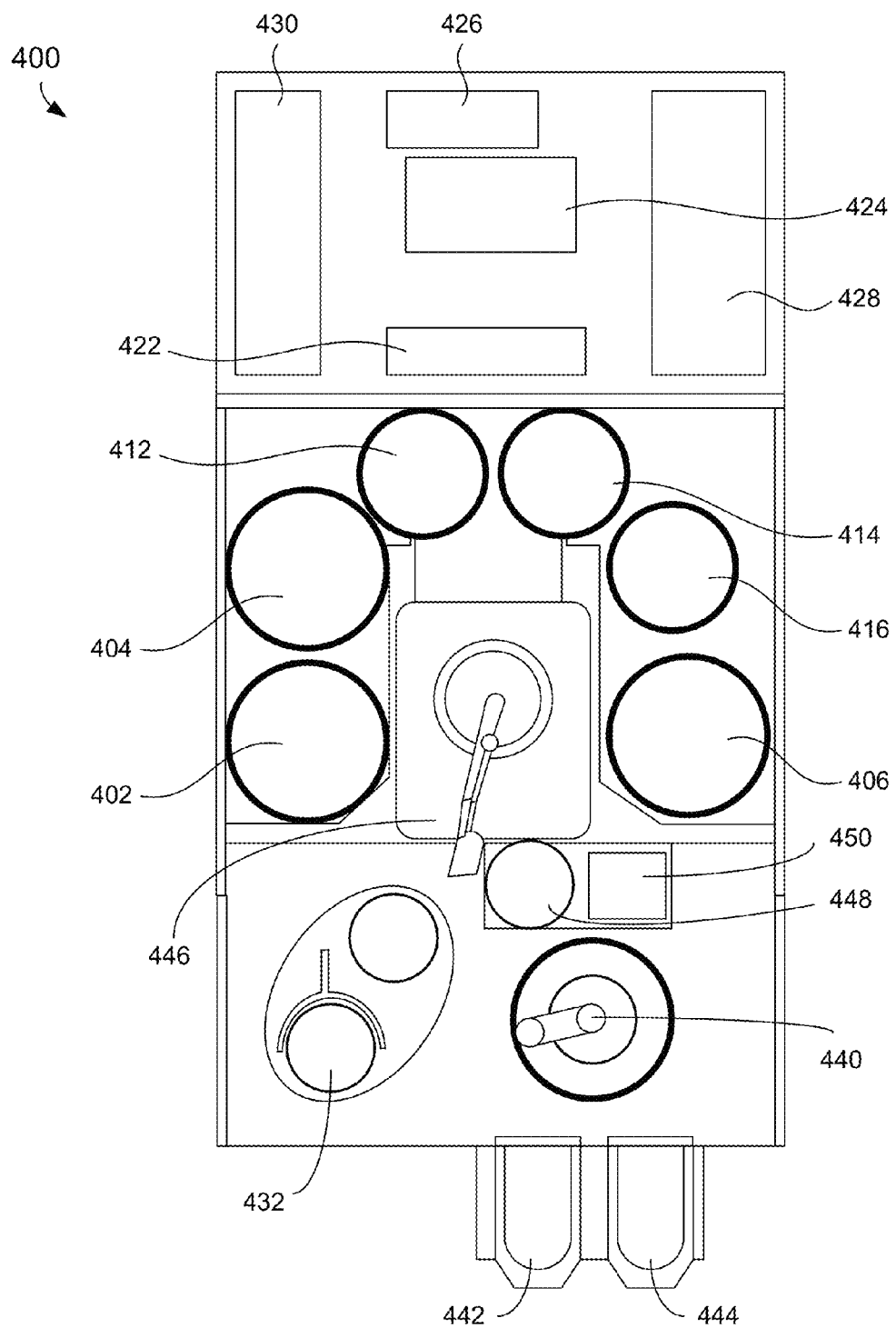
FIGS. 4 and 5 present example multi-tool apparatuses that may be used to implement the disclosed embodiments.

FIG. 4 shows a schematic of a top view of an example electrodeposition apparatus. The electrodeposition apparatus 400 may include three separate electroplating modules 402, 404, and 406. The electrodeposition apparatus 400 can also include three separate modules 412, 414, and 416 configured for various other process operations. For example, in some embodiments, one or more of modules 412, 414, and 416 may be a spin rinse drying (SRD) module. In other embodiments, one or more of the modules 412, 414, and 416 may be post-electrofill modules (PEMs), each configured to perform a function, such as edge bevel removal, backside etching, and acid cleaning of substrates after they have been processed by one of the electroplating modules 402, 404, and 406.

The electrodeposition apparatus 400 includes a central electrodeposition solution reservoir 424. The central electrodeposition solution reservoir 424 is a chamber that holds the chemical solution used as the electroplating solution in the electroplating modules 402, 404, and 406. The electrodeposition apparatus 400 also includes a dosing system 426 that may store and deliver additives for the electroplating solution. A chemical dilution module 422 may store and mix chemicals to be used as an etchant. A filtration and pumping unit 428 may filter the electroplating solution for the central electrodeposition solution reservoir 424 and pump it to the electroplating modules. In certain embodiments, the electrodeposition apparatus 400 may further include a detection device (not shown) to detect metal deposits on parts of the electroplating apparatus, such as on a cup bottom. The apparatus 400 may also include an autocleaning nozzle or other hardware (not shown) to clean parts of the electrodeposition apparatus 400 (e.g., the cup bottom of a substrate holder).

A system controller 430 provides electronic and interface controls to operate the electrodeposition apparatus 400. The system controller 430 (which may include one or more physical or logical controllers) controls some or all of the properties of the electroplating apparatus 400. The system controller 430 typically includes one or more memory devices and one or more processors. The processor may include a central processing unit (CPU) or computer, analog and/or digital input/output connections, stepper motor controller boards, and other like components. Instructions for implementing appropriate control operations as described herein may be executed on the processor. These instructions may be stored on the memory devices associated with the system controller 430 or they may be provided over a network. In certain embodiments, the system controller 430 executes system control software.

The system control software in the electrodeposition apparatus 400 may include instructions for controlling the timing, mixture of electrolyte components (including the concentration of one or more electrolyte components), inlet pressure, plating cell pressure, plating cell temperature, substrate temperature, current and potential applied to the substrate and any other electrodes, substrate position, substrate rotation, and other parameters of a particular process performed by the electrodeposition apparatus 400.

The system control logic may also include instructions for moving an autocleaning system into a cleaning position and performing an autocleaning method. Also, the system control logic may include instructions for moving a detection mechanism into position and performing the detection method. The controller may be programmed, in certain implementations, to initiate detection after a cleaning process is completed or at some other time or frequency. Detection instructions may include instructions for turning on a detector, rotating the electroplating apparatus (or part thereof) with respect to the detector, and recording a signal from the detector. The control logic may further include logic for interpreting a signal from the detector to determine if the cup bottom is sufficiently clean (i.e., whether the cup bottom is free of detectable deposits) to continue plating additional wafers. Additionally, the control logic may include instructions for returning a cleaning system and/or detection mechanism to a park position after the cleaner/detector are no longer needed.

The control logic may include instructions for performing one or more remedial actions in response to a detection that the cup bottom contains a metal deposit or is otherwise dirty. For example, the controller may sound an alarm or otherwise alert an operator in response to a determination that a deposit is present. Alternatively or in addition, the controller may take the electroplating cell offline in response to a determination that a cup bottom deposit is present. In some cases the controller may reinitiate the autoclean or other cleaning process in response to a determination that a deposit is present. One example of a cleaning/detecting sequence is an automated nitric acid cleaning spray, a cup and cup bottom rinse, and cup bottom plating re-detection, followed by return to on line conditions. In certain cases, the controller may indicate to an operator that manual cleaning is required.

System control logic may be configured in any suitable way. For example, various process tool component subroutines or control objects may be written to control operation of the process tool components necessary to carry out various process tool processes. System control software may be coded in any suitable computer readable programming language. The logic may also be implemented as hardware in a programmable logic device (e.g., an FPGA), an ASIC, or other appropriate vehicle.

In some embodiments, system control logic includes input/output control (IOC) sequencing instructions for controlling the various parameters described above. For example, each phase of an electroplating process may include one or more instructions for execution by the system controller 430. The instructions for setting process conditions for an immersion process phase may be included in a corresponding immersion recipe phase, for example. Similarly, separate recipes may be provided for a plating phase, and autoclean phase, a wafer holder inspection phase, etc. In some embodiments, the electroplating recipe phases may be sequentially arranged, so that all instructions for an electroplating process phase are executed concurrently with that process phase.

The control logic may be divided into various components such as programs or sections of programs in some embodiments. Examples of logic components for this purpose include a substrate positioning component, an electrolyte composition control component, a pressure control component, a heater control component, a potential/current power supply control component, an autoclean component, and a wafer holder inspection component.

In some embodiments, there may be a user interface associated with the system controller 430. The user interface may include a display screen, graphical software displays of the apparatus and/or process conditions, and user input devices such as pointing devices, keyboards, touch screens, microphones, etc.

In some embodiments, parameters adjusted by the system controller 930 may relate to process conditions. Non-limiting examples include bath conditions (temperature, composition, and flow rate), substrate position (rotation rate, linear (vertical) speed, angle from horizontal) at various stages, etc. These parameters may be provided to the user in the form of a recipe, which may be entered utilizing the user interface.

Signals for monitoring the process may be provided by analog and/or digital input connections of the system controller 430 from various process tool sensors. The signals for controlling the process may be output on the analog and digital output connections of the process tool. Non-limiting examples of process tool sensors that may be monitored include mass flow controllers, pressure sensors (such as manometers), thermocouples, optical position sensors, metal deposit detectors (such as optical reflective intensity detectors, eddy current sensors, or rolling resistance detectors), etc. Appropriately programmed feedback and control algorithms may be used with data from these sensors to maintain process conditions, both for plating and non-plating operations.

In one embodiment, the instructions can include inserting the substrate in a wafer holder, tilting the substrate, biasing the substrate during immersion, electrodepositing a tin/silver material on a substrate, moving a detection mechanism into position, and detecting whether metal deposits are present on the cup bottom.

A hand-off tool 440 may select a substrate from a substrate cassette such as the cassette 442 or the cassette 444. The cassettes 442 or 444 may be front opening unified pods (FOUPs). A FOUP is an enclosure designed to hold substrates securely and safely in a controlled environment and to allow the substrates to be removed for processing or measurement by tools equipped with appropriate load ports and robotic handling systems. The hand-off tool 440 may hold the substrate using a vacuum attachment or some other attaching mechanism.

The hand-off tool 440 may interface with a wafer handling station 432, the cassettes 442 or 444, a transfer station 450, or an aligner 448. From the transfer station 450, a hand-off tool 446 may gain access to the substrate. The transfer station 450 may be a slot or a position from and to which hand-off tools 440 and 446 may pass substrates without going through the aligner 448. In some embodiments, however, to ensure that a substrate is properly aligned on the hand-off tool 446 for precision delivery to an electroplating module, the hand-off tool 446 may align the substrate with an aligner 448. The hand-off tool 446 may also deliver a substrate to one of the electroplating modules 402, 404, or 406 or to one of the three separate modules 412, 414, and 416 configured for various process operations.

An apparatus configured to allow efficient cycling of substrates through sequential plating, rinsing, drying, and PEM process operations may be useful for implementations for use in a certain plating systems such as those that electroplate copper. To accomplish this, the module 412 can be configured as a spin rinse dryer and an edge bevel removal chamber. With such a module 412, the substrate would only need to be transported between the electroplating module 404 and the module 412 for the plating and EBR operations.

Figure 5:
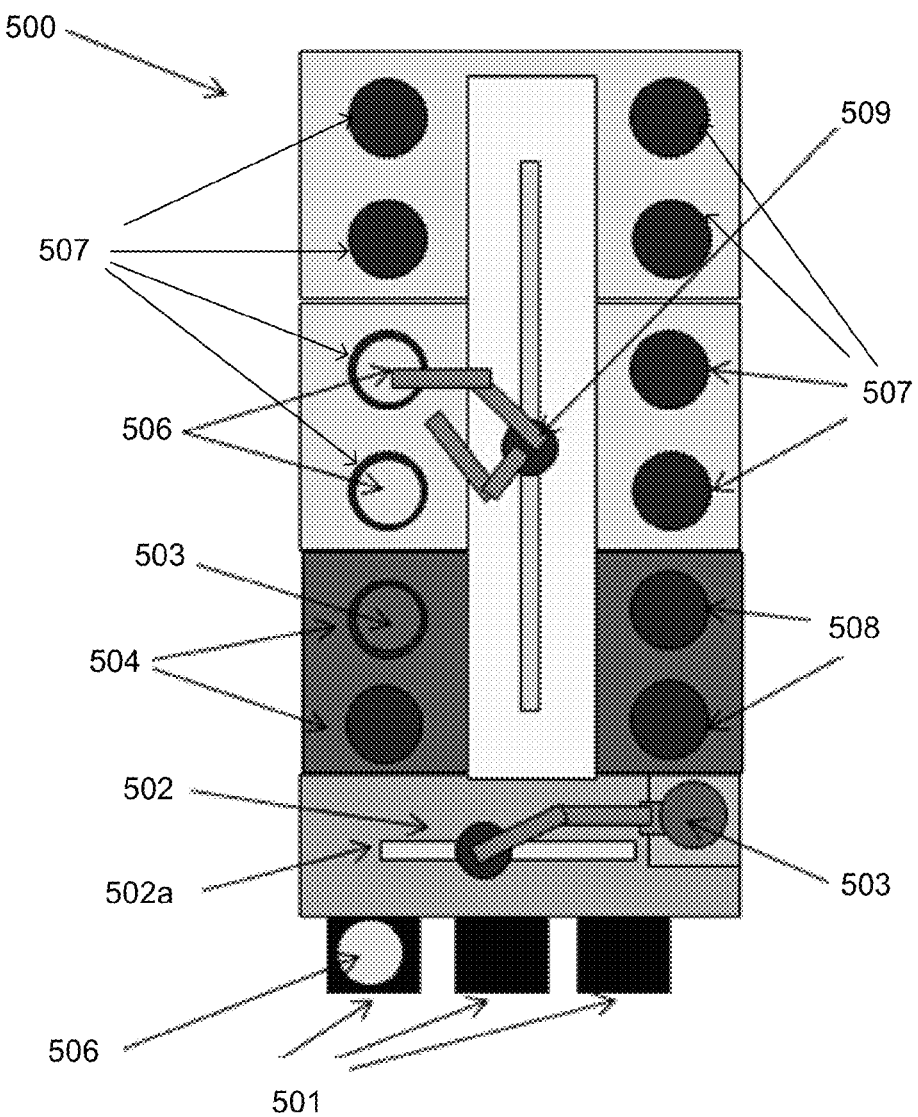

An alternative embodiment of an electrodeposition apparatus 500 is schematically illustrated in FIG. 5. In this embodiment, the electrodeposition apparatus 500 has a set of electroplating cells 507, each containing an electroplating bath, in a paired or multiple "duet" configuration. In addition to electroplating per se, the electrodeposition apparatus 500 may perform a variety of other electroplating related processes and sub-steps, such as spin-rinsing, spin-drying, metal and silicon wet etching, electroless deposition, electrolytic polishing (electropolishing), pre-wetting and pre-chemical treating, reducing, annealing, photoresist stripping, and surface pre-activation, for example. The electrodeposition apparatus 500 is shown schematically looking top down in FIG. 5, and only a single level or "floor" is revealed in the figure, but it is to be readily understood by one having ordinary skill in the art that such an apparatus, e.g. the Lam Research Sabre™ 3D tool, can have two or more levels "stacked" on top of each other, each potentially having identical or different types of processing stations.

Referring once again to FIG. 5, the substrates 506 that are to be electroplated are generally fed to the electrodeposition apparatus 500 through a front end loading FOUP 501 and, in this example, are brought from the FOUP to the main substrate processing area of the electrodeposition apparatus 500 via a front-end robot 502 that can retract and move a substrate 506 driven by a spindle 503 in multiple dimensions from one station to another of the accessible stations—two front-end accessible stations 504 and also two front-end accessible stations 508 are shown in this example. The front-end accessible stations 504 and 508 may include, for example, pre-treatment stations, and spin rinse drying (SRD) stations. Lateral movement from side-to-side of the front-end robot 502 is accomplished utilizing robot track 502a. Each of the substrates 506 may be held by a cup/cone assembly (not shown) driven by a spindle 503 connected to a motor (not shown), and the motor may be attached to a mounting bracket 509. Also shown in this example are the four "duets" of electroplating cells 507, for a total of eight electroplating cells 507. The electroplating apparatus may also include a detection mechanism (not shown) to detect metal deposits on areas of the electroplating apparatus, e.g., on the cup bottom. The electroplating cells 507 may be used for electroplating copper, nickel, tin-silver alloys, etc. A system controller (not shown) may be coupled to the electrodeposition apparatus 500 to control some or all of the properties of the electrodeposition apparatus 500. The system controller may be programmed or otherwise configured to execute instructions according to processes described earlier herein.

The electroplating apparatus/methods described herein-above may be used in conjunction with lithographic patterning tools or processes, for example, for the fabrication or manufacture of semiconductor devices, displays, LEDs, photovoltaic panels and the like. Generally, though not necessarily, such tools/processes will be used or conducted together in a common fabrication facility. Lithographic patterning of a film generally comprises some or all of the following steps, each step enabled with a number of possible tools: (1) application of photoresist on a work piece, i.e., a substrate, using a spin-on or spray-on tool; (2) curing of photoresist using a hot plate or furnace or UV curing tool; (3) exposing the photoresist to visible, UV, or x-ray light with a tool such as a wafer stepper; (4) developing the resist so as to selectively remove resist and thereby pattern it using a tool such as a wet bench; (5) transferring the resist pattern into a deposited pattern of pillars or other structures (e.g., tin silver solder structures) by electroplating; and (6) removing the resist using a tool such as an RF or microwave plasma resist stripper.

What is claimed is:

1. A method for detecting the presence or absence of metal deposits on a surface of a non-conductive portion of a substrate holder of an electroplating apparatus, comprising:
rotating a swing arm to position a detection hardware proximate a detection region on the substrate holder, wherein the substrate holder comprises a bottom and an interior edge; and
operating the detection hardware to detect the presence or absence of metal deposits in the detection region on the substrate holder, wherein the detection region is an annular region on the bottom of the substrate holder that extends at least about 5 mm or more from the interior edge of the substrate holder.

2. The method of claim 1, wherein the deposits comprise metals having significantly different reduction potentials.

3. The method of claim 1, wherein operating the detection hardware occurs after a certain number of substrates have been processed using the substrate holder, after a certain amount of charge has passed during deposition on substrates using the substrate holder, or after a certain amount or thickness of metal has been deposited on substrates using the substrate holder.

4. The method of claim 1, wherein positioning the detection hardware proximate the substrate holder comprises moving the detection hardware from a first position that is not under the substrate holder to a second position that is under the substrate holder, and further comprising moving the detection hardware from the second position after operating the detection hardware to detect the presence or absence of metal deposits.

5. The method of claim 4, further comprising raising an alarm, taking the electroplating apparatus offline, initiating a cleaning operation, or some combination thereof, in response to the detecting the presence of metal deposits in the detection region.

6. The method of claim 1, wherein operating the detection hardware comprises shining a source light on the detection region of the substrate holder and measuring a reflected light that reflects off the detection region of the substrate holder.

7. The method of claim 6, wherein shining a source light on the detection region of the substrate holder comprises shining a light that is complementary in color to a color of the detection region.

8. The method of claim 1, wherein operating the detection hardware comprises:
flowing an alternating current through a circular primary excitation coil positioned near the detection region to thereby generate a changing magnetic field that interacts with the detection region to produce eddy currents; and
monitoring the phase and/or magnitude of the eddy currents to detect the presence or absence of metal deposits.

9. The method of claim 8, wherein the monitoring is done with a receiver coil that is distinct from the primary excitation coil.

10. The method of claim 1, wherein operating the detection hardware comprises:
providing two or more electrical contacts that contact the detection region, wherein there is an electrical connection between the two or more electrical contacts;
flowing current through at least one electrical contact such that when the metal deposit is present in the detection region between the two or more electrical contacts, the metal deposit completes a circuit between the two or more electrical contacts, and when the metal deposit is not present in the detection region between the two or more electrical contacts, there is no complete circuit between the two or more electrical contacts; and
measuring an electrical property to detect the presence or absence of the metal deposit in the detection region.

11. An apparatus for detecting the presence or absence of a metal deposit on a substrate holder of an electroplating apparatus, comprising:
detection hardware positioned on mounting hardware,
wherein the mounting hardware comprises a swing arm that swings into place to bring the detection hardware proximate a detection region on the substrate holder, the substrate holder comprising a bottom and an interior edge, wherein the detection region on the substrate holder is on the bottom of the substrate holder extending about 5 mm or more from the interior edge of the substrate holder, and
wherein the detection hardware is configured to detect the presence or absence of a metal deposit in the detection region of the substrate holder.

12. The apparatus of claim 11, wherein the mounting hardware is integral with an electroplating apparatus.

13. The apparatus of claim 11, wherein the apparatus for detecting the presence or absence of a metal deposit can interact with a plurality of substrate holders.

14. The apparatus of claim 11, wherein the mounting hardware further comprises a cleaning assembly for removing metal deposits from the substrate holder.

15. The apparatus of claim 11, wherein the detection hardware comprises a light source and a light detector, wherein the light source is configured to shine light on the detection region of the substrate holder, and wherein the light detector is configured to measure light that is reflected off the detection region of the substrate holder.

16. The apparatus of claim 15, further comprising a filter positioned between the detection region and the light source, or between the detection region and the detector, that filters out wavelengths of light that are normally reflected by the detection region when no metal deposits are present.

17. The apparatus of claim 15, further comprising one or more optical fibers to carry light between the light source and an optical outlet that shines on the detection region and/or between an optical inlet positioned proximate the detection region and the light detector.

18. The apparatus of claim 17, wherein the optical outlet that shines on the detection region and the optical inlet positioned proximate the detection region are provided together as an integrated bundle of optical fibers.

19. The apparatus of claim 11, wherein the detection hardware comprises a circular primary excitation coil through which an alternating current flows to thereby generate a changing magnetic field that interacts with the detection region to produce eddy currents.

20. The apparatus of claim 11, wherein the detection hardware comprises two or more electrical contacts that contact the detection region, and an electrical connection between the two or more electrical contacts, such that when a metal deposit is present in the detection region between the two or more electrical contacts, an electrical circuit is complete, but when a metal deposit is not present in the detection region between the two or more electrical contacts, the electrical circuit is incomplete.

21. The apparatus of claim 11, wherein the substrate holder comprises a cup and a lip seal, wherein the bottom and interior edge of the substrate holder are the bottom and interior edge of the cup, wherein the cup comprises a vertical inner surface extending upwards from the interior edge of the cup, and wherein the lip seal is positioned at the top of the vertical inner surface.

\* \* \* \* \*